United States Patent [19]

Kuipers

[11] Patent Number: Plant 7,712

[45] Date of Patent: Nov. 12, 1991

[54] SPATHIPHYLLUM PLANT NAMED SNOW WHITE

[75] Inventor: Nico J. Kuipers, De Kwakel, Netherlands

[73] Assignee: Reginald Deroose, Belgium

[21] Appl. No.: 520,356

[22] Filed: May 7, 1990

[51] Int. Cl.[5] ..... H01H 5/00

[52] U.S. Cl. ..... Plt./88

[58] Field of Search ..... Plt./88

*Primary Examiner*—Howard J. Locker

*Attorney, Agent, or Firm*—Foley & Lardner

[57] ABSTRACT

A distinct Spathiphyllum plant named Snow White characterized by its compact growth habit and short plant height, long flower stems which extend well above the foliage, relatively short and narrow leaves, small white flowers, uniform flowering, and the impressing of alternate veins on the upper surface of its leaves.

2 Drawing Sheets

The present invention comprises a new and distinct cultivar of Spathiphyllum, botanically known as Spathiphyllum and referred to by the cultivar name Snow White.

The new cultivar is a product of a planned breeding program, and was originated from a cross made by the inventor during such a program in De Kwakel, The Netherlands in 1988.

Both the female or seed parent, and the male or pollen parent, were unnamed and presently unknown seedlings. Snow White was discovered and selected as a flowering plant within the progeny of the stated cross by the inventor on Aug. 9, 1988, in a controlled environment in De Kwakel, The Netherlands. Subsequent asexual reproduction of the new cultivar by tissue culture has demonstrated that the combination of characteristics as herein disclosed for the new cultivar are firmly fixed and are retained through successive generations of asexual reproduction.

The following traits have been repeatedly observed and in combination distinguish Snow White as a new and distinct cultivar:

1. A very compact habit. The plant is about 30 cm high, and the leaves are smaller than other Spathiphyllums, being approximately 20 cm long and 7 cm wide.
2. Snow White forms numerous side shoots.
3. The white flowers of Snow White are relatively large, particularly in view of its compact habit.
4. Upright leaves, which are rather narrow and pointed.
5. Uniform flowering.
6. The flower stems are relatively long compared with the compact nature of the plant, with the flower stems extending about 15 cm above the upper leaves.
7. Alternate veins are slightly impressed on the upper surface of the leaf.

The following observations, measurements and values describe plants grown in De Kwakel, The Netherlands under greenhouse conditions which closely approximate those generally used in horticultural practice. Color references are made to The Royal Horticultural Society (R.H.S.) Colour Chart, except where general color terms of ordinary significance are used. The color values were determined between 8:30–9:00 on Nov. 6, 1989 under bright but slightly cloudy daylight conditions at Aalsmeer, The Netherlands.

In the color photographic drawings, Sheet 1 is a top perspective view of Snow White. Sheet 2 is a perspective view of reduced size, showing more vividly the compact plant growth habit, long flower stems, and flowers of Snow White.

The new cultivar can be compared in certain respects to the Spathiphyllum cultivar Palace, although there is a marked difference in the height of the respective cultivars. Similarities in the cultivars are the color of the leaves and the flowers, and veins that are impressed on the upper surface of the leaf. Differences between the respective cultivars are the relatively wide leaves of Palace (approximately 25 cm long, 10 cm wide), the thicker but shorter flower stems of Palace, and the substantially greater plant height of Palace.

The new cultivar Snow White can also be compared to the Spathiphyllum cultivar Petite, which also has a short habit. The cultivars have several differing characteristics, with Petite having a thinner leaf (approximately 6 cm), a small flower (7 cm long and 4 cm wide), and elongated flower stems (up to 50 cm).

Classificaiton:

*Botanical.*—Spathiphyllum cv Snow White.

*Commercial.*—Spathiphyllum.

Parentage:

*Male parent.*—Unnamed seedling.

*Female parent.*—Unnamed seedling.

Propagation: The preferred form of vegetative propagation is by tissue culture.

Plant: After the first flower appears approximately three (3) months after potting in 10 cm pots, the plant is approximately 30 cm high, measured from the top of the pot. Six (6) to eight (8) weeks later, the second flower appears and the plant at that stage of growth, and thereafter, is 40 to 45 cm tall, measured from the top of the pot. The plant is approximately 30 cm in diameter when fully grown.

*Growth habit.*—Short.

Leaves:

*Form and size.*—Narrowly elliptic. Length: 20 cm. Width: 7 cm.

*Texture.*—Leathery, upper surface is glossy.

*Veins.*—Alternate veins slightly impressed on upper surface.

*Color.*—Upper surface: Slightly darker than 137A. Lower surface: 137 B but slightly more grey.

Flower:

*Buds.*—Formed in leaf axil.

Spathe:

*Size.13* Large, approximately 10 cm long and 6 cm wide.

*Color* (R.H.S.)—155D.

*Shape.*—Oval.

*Flowering.*—Flowers repeatedly.

Spadix:

*Size.*—4-5 cm in length.

*Color* (R.H.S.)—158A

*Longevity.*—2 to 3 months.

Reproductive Organs:

*Stamens.*—White in color, normal.

*Anthers and filaments.*—White in color, normal.

*Pollen*—White, normal.

*Pistils.*—White, normal.

Roots: White in color; normal root system.

Disease Resistance: No disease problems noted to date.

I claim:

1. A new and distinct Spathiphyllum plant named Snow White, as described. and illustrated.

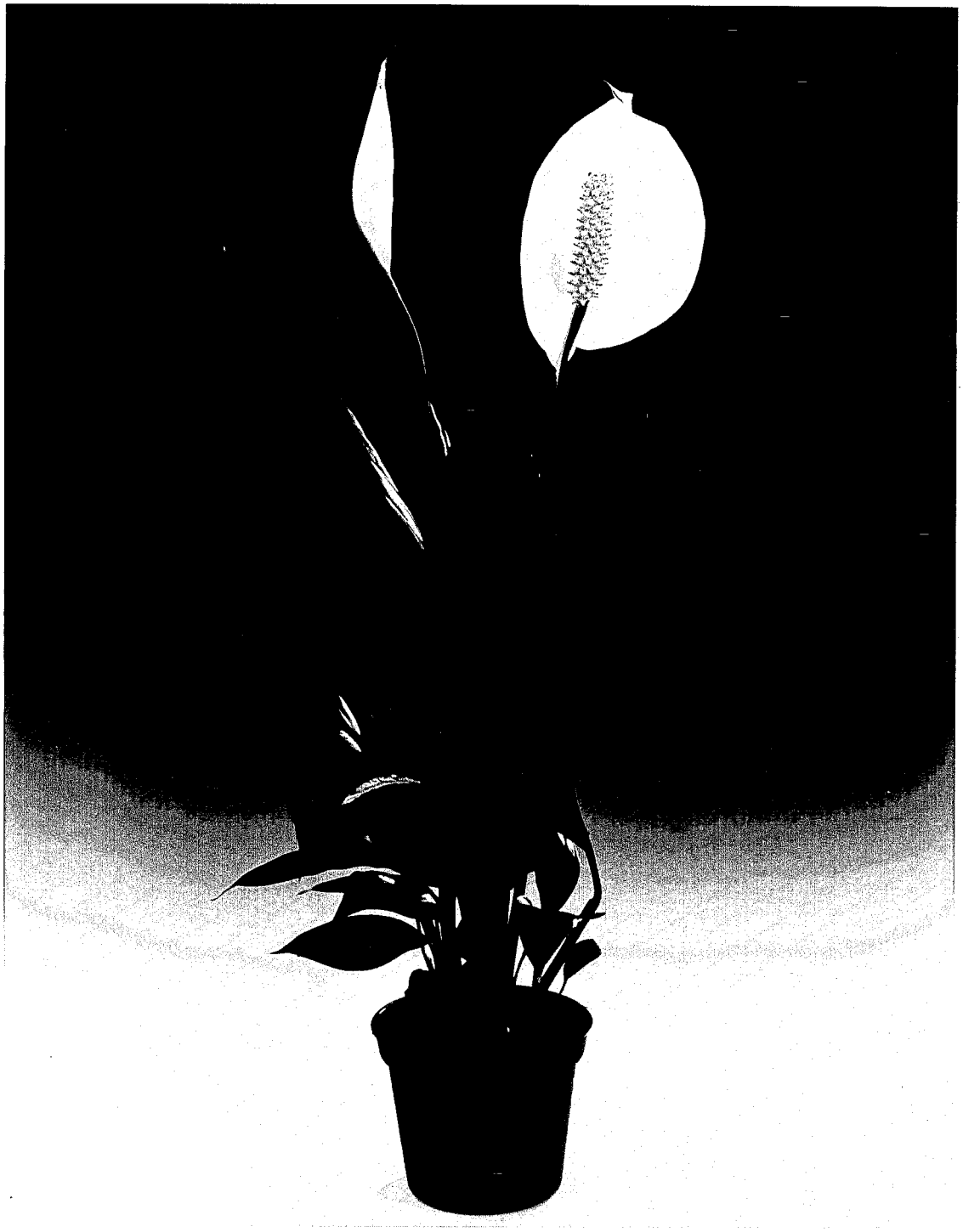

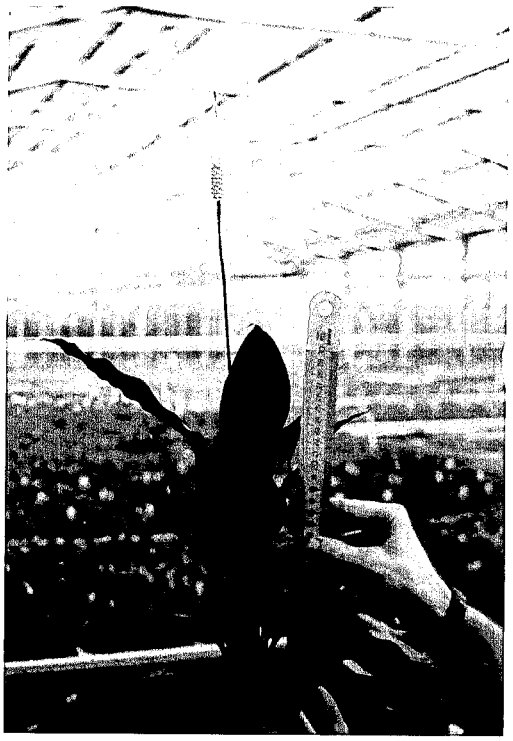

* * * * *